United States Patent [19]

Leininger

[11] Patent Number: 4,730,606

[45] Date of Patent: Mar. 15, 1988

[54] APPARATUS FOR APPLYING TRACTION DURING OSCILLATORY THERAPY

[75] Inventor: Peter A. Leininger, San Antonio, Tex.

[73] Assignee: Kinetic Concepts, Inc., San Antonio, Tex.

[21] Appl. No.: 944,245

[22] Filed: Dec. 17, 1986

Related U.S. Application Data

[63] Continuation-in-part of Ser. No. 821,276, Jan. 22, 1986, abandoned, which is a continuation-in-part of Ser. No. 560,258, Dec. 12, 1983, abandoned, which is a continuation of Ser. No. 389,767, Jun. 18, 1982, abandoned, which is a continuation of Ser. No. 134,774, Mar. 28, 1980, abandoned.

[51] Int. Cl.$^{4}$ .......................... A61F 5/04; A47D 9/02

[52] U.S. Cl. .......................................... 128/75; 5/109; 128/84 C

[58] Field of Search .................. 128/24 R, 33, 70–75, 128/84 R, 84 B, 84 C; 5/109; 272/73

[56] References Cited

U.S. PATENT DOCUMENTS 1,205,649 11/1916 Miller .................................... 128/72
2,297,861 10/1942 Coin .................................. 128/84 C
2,949,110 8/1960 Lee ....................................... 128/75

FOREIGN PATENT DOCUMENTS 920448 1/1947 France ............................. 128/84 C
592632 9/1947 United Kingdom .............. 128/84 C

OTHER PUBLICATIONS

The Roto Rest Kinetic Treatment Tables, (Mark I and III Instruction Manual; p. 59.
Green, B., "Kinetic Nursing for Spinal Cord Injuries", reprinted from Paraplegia Life, Jan.-Feb. 1976, including photographs of Roto Rest Mark I and Roto Rest Mark II Beds.
Roto Rest Promotional Brochure.
New Product Bulletin, Medical Equipment Distributors, Inc., Special Issue:
Introducing Roto Rest Mark I, the New Concept in Patient Care, Bulletin No. 9, (Sep. 1975).
Roto Rest Mark I Automatically Controlled Kinetic Nursing Operating Instructions Manual (undated).
Experimental Data Traction Force During Oscillatory Therapy (untitle, undated).
The Roto Rest Mark III Kinetic Treatment Table for Complications of Immobility, promotional brochure (undated).
Keane Roto Rest Mark III and IV promotional brochure (undated).
Mark I Accessory: New Traction Device Makes Kinetic Therapy a Reaility for Multiple Trauma and Orthopedic Patients, advertising layout (undated).
The Roto Rest Mark I Kinetic Treatment Table, Effective Prevention, Proven Therapy, for Complications of Immobility, advertising brochure (undated).
Keane Mobility Bed Trauma and Intensive Care Unit, advertising brochure (undated).
Roto Rest Mark II pictorial display (undated).
Roto Rest promotional brochure (undated).

*Primary Examiner*—Clyde T. Coughenour
*Attorney, Agent, or Firm*—Cox & Smith Inc.

[57] ABSTRACT

The invention is to an apparatus for applying traction to an immobilized patient undergoing oscillatory therapy. The support means for weights has a portion on an oscillating support platform of the bed and part stationary beyond the oscillating portion with a cable contained partially within a conduit thereinbetween offset from the longitudinal center line of oscillating patient support.

4 Claims, 5 Drawing Figures

APPARATUS FOR APPLYING TRACTION DURING OSCILLATORY THERAPY

BACKGROUND OF THE INVENTION

The present application is a continuation-in-part application of my co-pending application Ser. No. 821,276, filed on Jan. 22, 1986, which was a continuation-in-part application of application Ser. No. 560,258, filed on Dec. 12, 1983, which was a continuation application of application Ser. No. 389,767, filed on June 18, 1982, which was itself a continuation application of application Ser. No. 134,774, filed on Mar. 28, 1980 all now abandoned.

This invention relates to an apparatus and method for applying traction to an immobilized patient undergoing oscillatory therapy. In particular, it relates to a traction device for a bed which provides controlled oscillatory movement to a bed support means and a patient disposed thereon.

It is known in the art to provide a bed with a patient support means adapted for a controlled oscillatory movement whereby a patient may be subjected to gentle alterations of position while lying on the bed support means. Beds having oscillatory patient support platforms are shown in U.S. Pat. Nos. 3,343,165, issued to F. X. Keene on Mar. 25, 1969, and U.S. Pat. No. 4,175,550, issued to James R. Leininger et al. on Nov. 27, 1979, which patents are incorporated herein in toto for any and all purposes by this specific reference thereto. The support beds of the above named patents provide oscillatory treatment to substantially lessen, if not eliminate, the problems and complications of immobilized patients.

In the case of multiple trauma and orthopedic patients, it may be desirable to provide traction in combination with oscillatory treatment. The combination of traction and oscillatory therapy would make it possible to provide beneficial oscillatory therapy to a much broader range of immobilizing conditions. Applying oscillatory treatment in combination with traction can drastically reduce the incidence of immobility-caused complications such as hypostatic pneumonia, pressure sores, venous thrombosis, pulmonary emboli and the like in some patients. For the supine or non-operative patient confined to long-term bed rest, the oscillating bed has been advocated to reduce those complications by continuously turning the patient from side-to-side through an arc of about 124°. Keane, F. X., Roto Rest, 7 Paraplegia 254 (1970). The oscillating bed is potentially beneficial for numerous orthopedic applications. It is, however, a poor platform for conventional traction configurations.

So far as known, it has been a practice in the past to use adjustable spring means connected with the patient support platform to apply traction to the immobilized patient on the oscillatory treatment bed support platform. The spring means is generally used to provide a substantially constant traction force. The use of the spring means to provide the traction generally requires that the patient remain in one position. When oscillatory treatment is being used in combination with the traction, any shifting of the patient may affect the amount of force exerted by the spring. Accordingly, the spring means is generally limited to upper arm traction to either side of the bed support platform when patient movement is less likely to affect the amount of traction force.

During traction without oscillatory treatment, substantially constant traction force can be achieved through the use of weights. However, during oscillatory therapy, the patient support platform, as well as the patient, are in constant motion due to the oscillation of the patient support platform. The constant motion of the patient support platform is, of course, translated to the weights at the end of the traction cable, causing them to cycle up and down as the support platform oscillates if the traction is applied in any direction other than along the center line of the patient support platform. When, for instance, cervical traction is applied along the center line of the patient support platform, which is also the patient's center line, the oscillation causes little or no difficulty. But when traction is applied at an oblique angle from the center line, as it would be if, for instance, traction is applied to the patient's leg, the weights can move so far as to strike the floor at one extreme and the bed frame at the other during each oscillation. Further, if traction is to be applied to more than one portion of the patient's body, there is but one center line, consequently traction forces must be applied at an angle relative to the center line.

Recent studies have discovered that the so-called constant traction of up to twenty-five pounds applied when the patient rests on a non-oscillating bed may vary by as much as 100% of the applied traction weight during such normal activities as patient movement, nursing procedures and changes in bed configuration. It is unlikely that these extreme changes occur at the fracture site, and they are most likely substantially dampened by muscle contraction and/or elastic deformation of the muscles and other soft tissues bridging the fracture site, because clinical observations indicate that patients generally maintain good alignment of a fracture despite these changes. However, it is clear that movement of traction weights as a result of oscillation of the patient support platform would impart additional changes in applied traction weight, especially when those weights strike the floor or hang up on the bed frame, the latter representing a potentially dangerous situation as a result of a drastic change in applied traction weight at the fracture site.

There is, therefore, a need for an apparatus which combines traction with oscillatory treatment and which is capable of maintaining a substantially constant traction force on the patient notwithstanding movement of the patient. There is also a need for an apparatus which provides for the application of substantially constant traction weight, even during oscillation of the patient support platform, and which does not transmit those oscillations to the weights.

SUMMARY OF THE INVENTION

Those needs are fulfilled by providing a traction apparatus for use in combination with a oscillating treatment bed comprising a generally vertical support mounted along the longitudinal center line of the oscillating patient support platform of an oscillating therapeutic bed for oscillation therewith, and having a generally horizontal, transverse support bar rigidly connected thereto. A support bar is mounted on the portion of the oscillating bed which does not oscillate with the oscillating support platform. A flexible cable is provided having a weight at one end and means for engaging a patient on the oscillating support platform at the other end, the cable being slidably received within a cable conduit. The cable conduit is connected between the transverse support bar and the support bar mounted on the portion of the oscillating bed which does not oscillate with the bed support platform, and transmits the constant downward force applied to the end of the cable by the weight into a substantially constant force on the patient engaging means at the other end of the cable during oscillation of the oscillating support platform.

BRIEF DESCRIPTION OF THE PREFERRED EMBODIMENT

Figure 1:
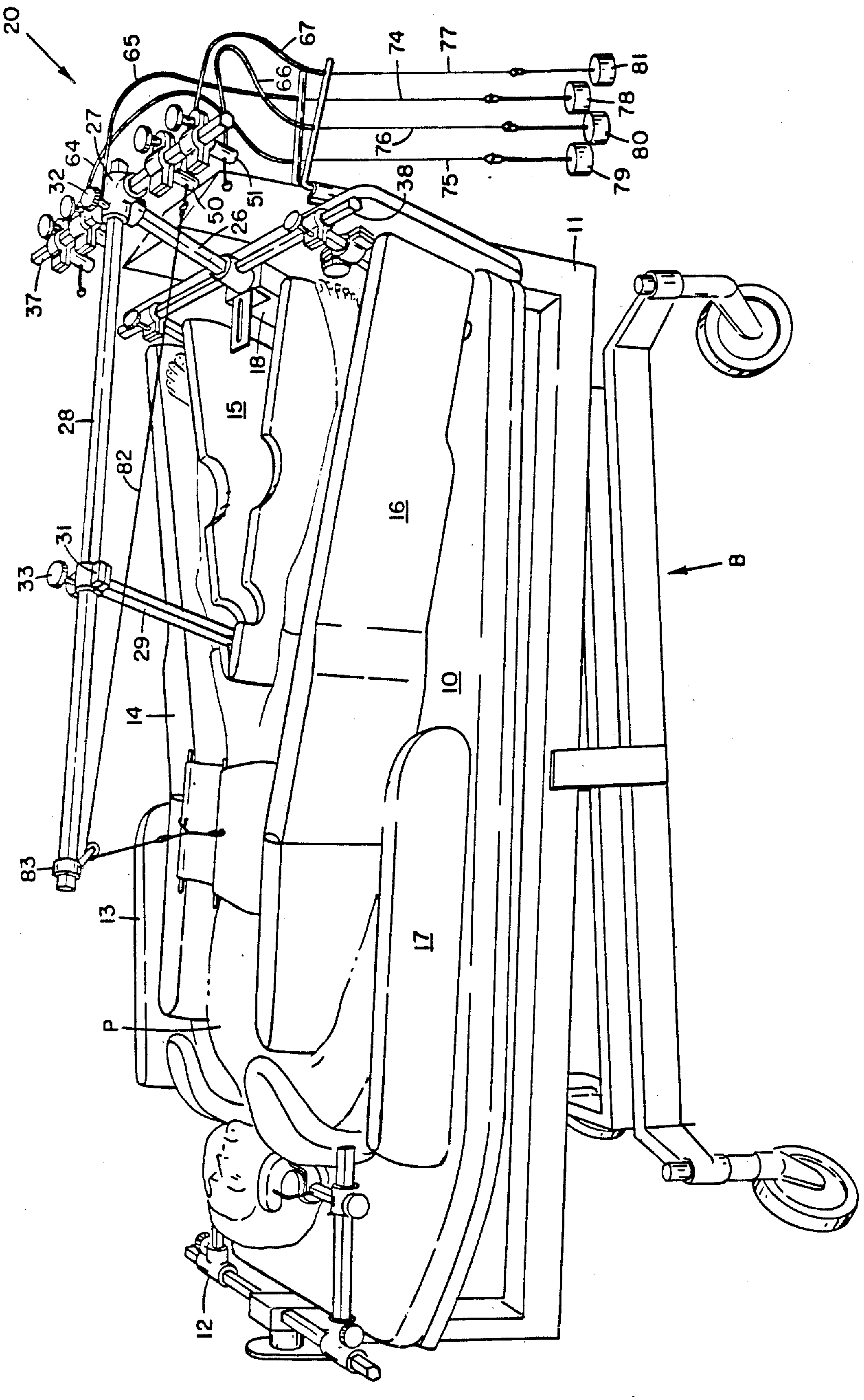
FIG. 1 is a side view in perspective of a therapeutic bed having an embodiment of the traction device of the invention mounted thereon and connected with the patient.

Referring to FIG. 1 there is shown a therapeutic bed B of the type shown in U.S. Pat. Nos. 3,434,165 and 4,175,550 which have been incorporated herein. The therapeutic bed B includes an oscillating patient support platform 10 mounted for oscillation relative to support frame 11. A patient P is shown positioned on the platform 10. Head restraining means 12 and side restraining means 13, 14, 15, 16 and 17 are provided to restrain the patient on the bed during oscillation. Traction device 20 is shown mounted at the foot of the bed.

Figure 2:
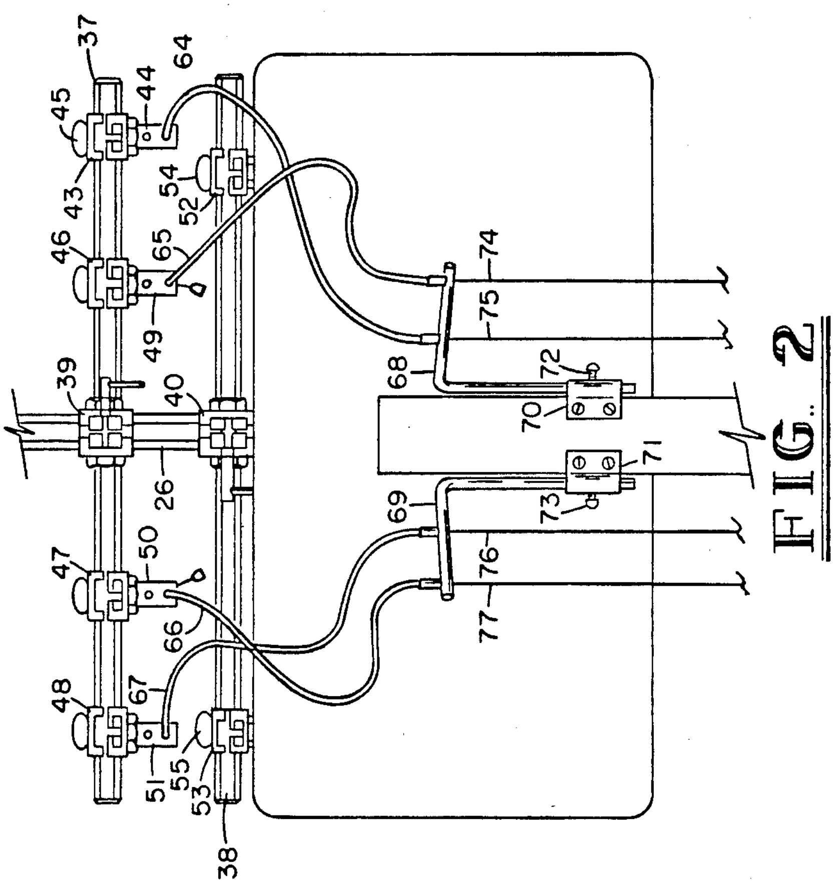
FIG. 2 is a partial view of the cable device of the invention viewed from the foot of the therapeutic bed.
Figure 3:
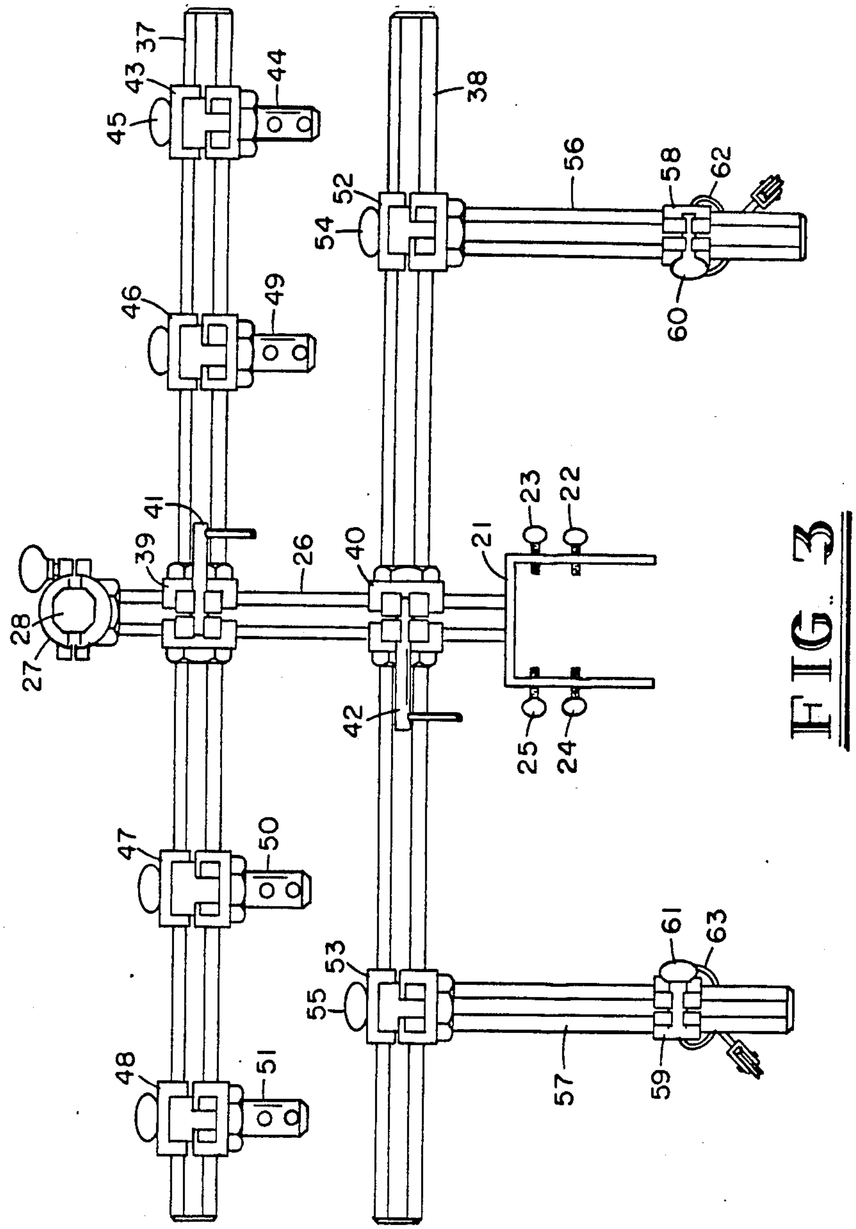
FIG. 3 is a partial view of the traction device of the invention.
Figure 4:
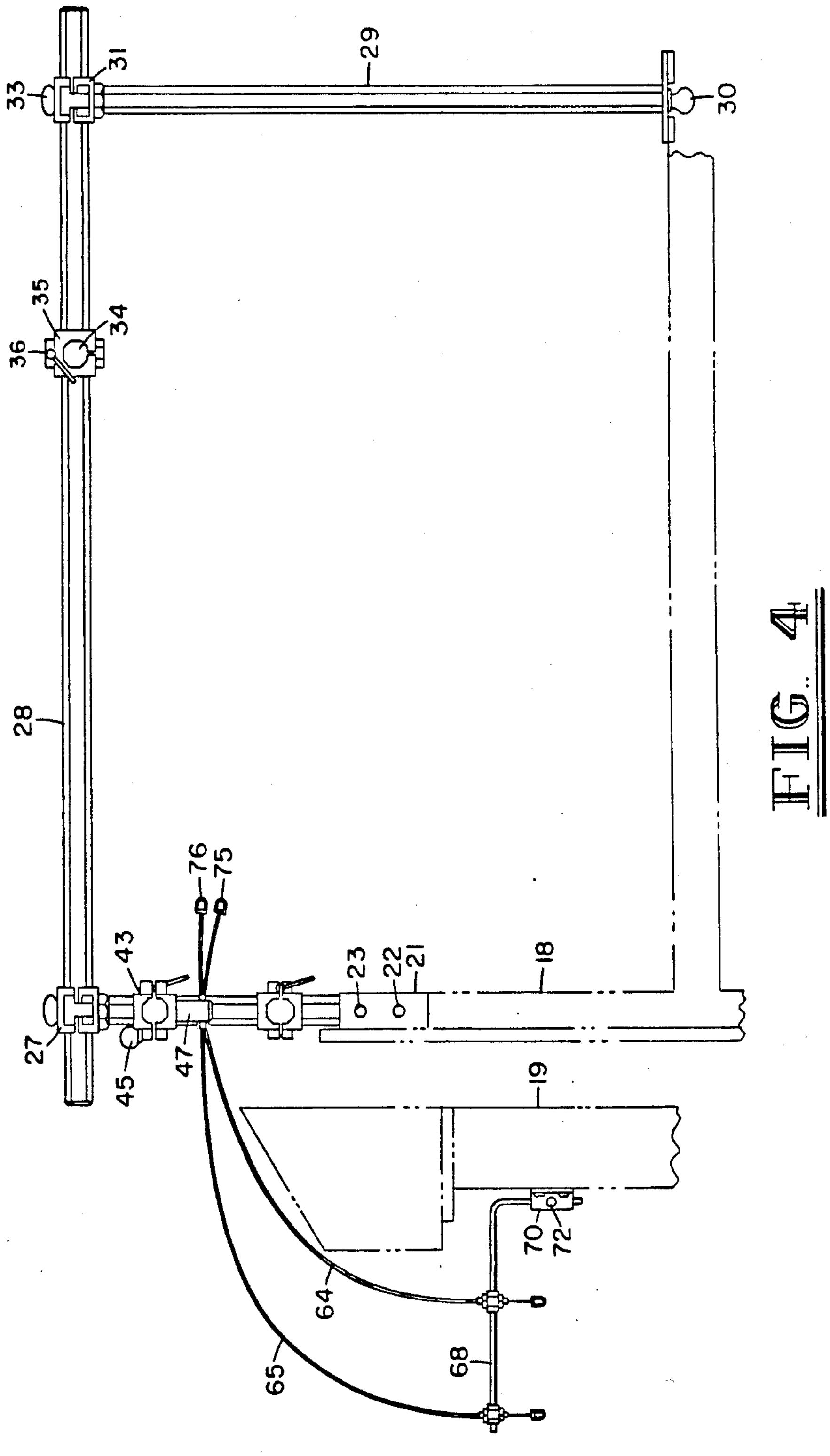
FIG. 4 is a partial side view of an embodiment of the traction device of the invention showing how it is connected with a therapeutic bed.
Figure 5:
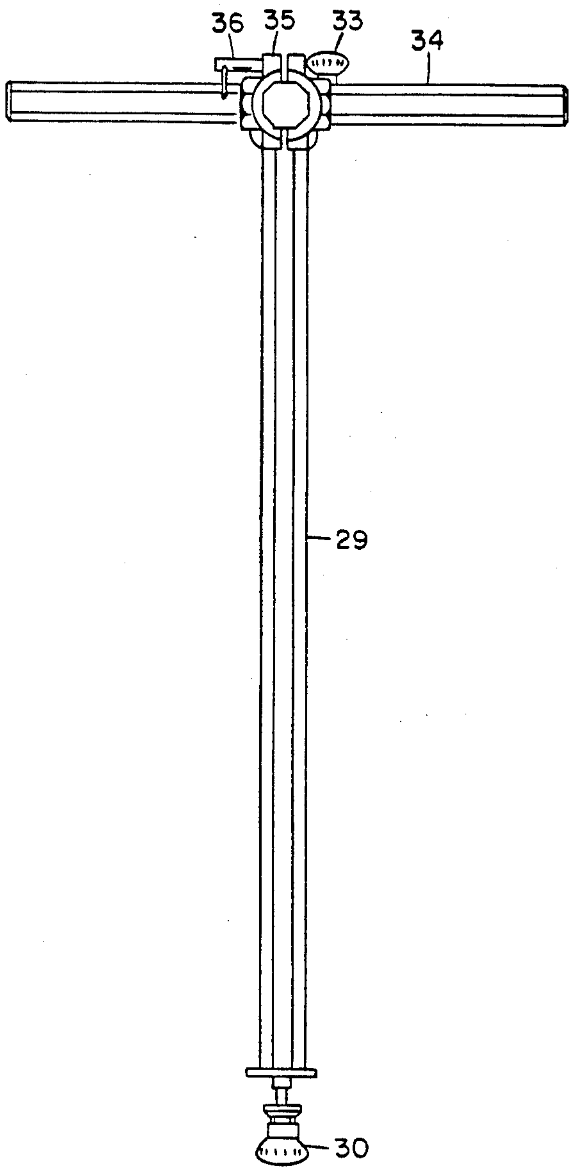
FIG. 5 is an elevation view of a vertical support member which is connected to the patient's support platform and having a lateral support connected therewith.

Traction device 20 includes a inverted U-shaped clamp member 21 as shown in FIG. 3 having a plurality of thumb screws 22, 23, 24 and 25. The clamp member 21 clamps over inner frame member 18 and is held in position by the thumb screws 22, 23, 24, and 25. A vertical support bar 26 is secured with the clamp member 21 and extends upwardly therefrom. The support bar 26 is preferably octagonal and uniform in cross section. A bracket member 27 is mounted at the upper end of the support bar 26 for connection with horizontal support bar 28 as best shown in FIGS. 1 and 2. The support bar 28 is also octagonal and uniform in cross section. A second vertical support bar 29 as best shown in FIGS. 4 and 5 is connected with the patient's support platform 10 with screw member 30. Bracket member 31 as shown in FIGS. 1 and 4 is secured at the upper end of the support bar 29 for clamping onto and supporting the horizontal support bar 28. As will be apparent, the bracket members 27 and 31 include screw tighteners 32 and 33 respectively so that the horizontal support bar 28 may be slidably positioned relative to the brackets and then clamped in position. A center support bar 34 as shown in FIGS. 4 and 5 may be slidably mounted upon the horizontal support bar 28 by clamping member 35 having a screw tightener 36. The bar 34 may be used to support traction means in various types of traction.

The vertical support bar 26 has two horizontal bars 37 and 38 slidably mounted thereon by clamp means 39 and 40 respectively. Screw tighteners 41 and 42 adjustably secure the clamp means to secure clamp means 39 and 40 respectively to a desired location on the vertical support bar 26.

A cable support 43 having a cable connector 44 as shown in FIGS. 2 and 3 is slidably mounted on the horizontal bar 37 and retained in position by screw tightener 45. Cable supports 46, 47 and 48 are identical to cable support 43 in that they are slidably mounted upon the horizontal support bar 37 and include cable connectors 49, 50 and 51 respectively.

Again referring to FIG. 3, slidable clamp brackets 52 and 53 having screw tighteners 54 and 55 are slidably mounted upon lower horizontal support bar 38. Downwardly extending support bars 56 and 57 are connected with the clamp brackets 52 and 53 respectively. Clamp brackets 58 and 59 having screw tightners 60 and 61 are slidably mounted upon the downward extending support bars 56 and 57 respectively. Suitable pulling means 62 and 63 are connected to the clamp brackets 58 and 59 for connecting with foot traction or the like as desired.

As best shown in FIGS. 1 and 2, cable conduits 64, 65, 66, and 67 are connected to the cable connectors 44, 49, 50 and 51. The lower ends of the cable conduits are connected to L-shaped support bars 68 and 69. The L-shaped support bars 68 and 69 are pivotally mounted to support brackets 70 and 71 which are secured to frame support member 19 by screws as shown or other suitable fasteners. The L-shaped support bars 68 and 69 are locked in position relative to the support bracket 70 and 71 by screws 72 and 73 respectively. The cable conduits 64, 65, 66, and 67 slidably receive cables 74, 75, 76 and 77.

Selected weight means 78, 79, 80, and 81 may be secured to the ends of the cables 74, 75, 76 and 77 respectively as required. Suitable traction cables 82 such as the cable shown in FIG. 1 may be secured to one of the cables and may be connected to a pulley member 83 which connects to a traction member such as pelvic sling 84. As will be apparent, the four cable supports 43, 46, 47 and 48 can be used for as many as four traction lines and additional cable supports and cables and pulley could also be added. The traction device could be used to provide such common traction as balanced traction, Buck's traction, split Russell's traction or any other type of suitable traction. The traction applied to the patient using the invention is substantially the same as that applied to a patient in a non-oscillating hospital bed. The difference is that the traction provided by the traction device of the invention can be used on a patient who is in an oscillating therapeutic bed. Through the use of pulleys and cables and the adjustable support bars, most common types of traction can be used on a patient in the oscillating bed, including traction applied at any angle relative to the center line of the patient support platform. Referring, for instance, to FIG. 1, horizontal support bar 28 is mounted in the center line of patient support platform 10, yet cable 82, having weight 81 on the end thereof, is connected to cable connector 50, and therefore exerts traction force at an angle which is oblique to that center line. The specific arrangement of the components would generally depend on known traction principles so further explanation is unnecessary for the description of the invention.

During operation, the patient support platform 10 oscillates in a predetermined arc. The horizontal support bar 37 upon which the cable supports are mounted likewise oscillates with the patient and the bed support platform. However, the motion of the patient and bed support platform does not affect the cables and the support bars 68 and 69 or the weights 78, 79, 80, and 81. Accordingly, movement of the patient on the bed does not affect the substantially constant force of the traction applied through the weights. Nor does the shifting of the patient which occurs during oscillating treatment affect the substantially constant forces applied by the weights.

Although the invention has been described in conjunction with the foregoing specific embodiment, many alternatives, variations and modifications are apparent to those of ordinary skill in the art. Those alternatives, variations and modifications are intended to fall within the spirit and scope of the appended claims.

What is claimed is:

1. A traction apparatus for an oscillating therapeutic bed having a non-oscillating portion and an oscillating patient support platform comprising:

a generally vertical support bar rigidly mounted to the oscillating patient support platform for oscillation therewith;

a generally horizontal, transverse support bar rigidly mounted to said vertical support bar;

a support bar mounted on the portion of the oscillating therapeutic bed which does not oscillate with the oscillating patient support platform of the oscillating therapeutic bed provided with one or more spaced cable support means to position force applying means spaced from the longitudinal center line of the oscillating patient support platform;

a cable having a weight at one end and means for engaging a patient lying on the oscillating patient support platform on the other end;

a cable conduit slidably receiving said cable, said cable conduit being connected at one end to said transverse support bar spaced from said longitudinal centerline and at the other end to said support bar mounted on the portion of the oscillating therapeutic bed which does not oscillate with the oscillating patient support platform and transmitting the constant downward force applied to the end of said cable by the weight into a substantially constant force on the patient engaging means.

2. The apparatus of claim 1 wherein said cable conduit is connected to said transverse support bar by a cable connector.

3. The apparatus of claim 2 wherein said cable connector is selectively positionable along said transverse support bar whereby the constant downward force applied to the end of said cable by the weight is exerted at an angle relative to the center line of the patient support platform.

4. The apparatus of claim 1 wherein a plurality of cables, weights and cable conduits are provided with said conduits connected at one end to said transverse support bar spaced from the longitudinal centerline and at the other end to said support bar mounted on the portion of said oscillating therapeutic bed which does not oscillate.

* * * * *